US00PP36643P2

(12) United States Plant Patent
Bédard

(10) Patent No.: US PP36,643 P2
(45) Date of Patent: May 6, 2025

(54) HYBRID TEA ROSE PLANT NAMED 'WEKselyan'

(50) Latin Name: *Rosa hybrida*
Varietal Denomination: WEKselyan

(71) Applicant: Early Morning LLC, Lawrenceburg, IN (US)

(72) Inventor: Christian Bédard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 18/957,357

(22) Filed: Nov. 22, 2024

(51) Int. Cl.
*A01H 5/02* (2018.01)
*A01H 6/74* (2018.01)

(52) U.S. Cl.
USPC ..... Plt./132
CPC ..... *A01H 6/749* (2018.05)

(58) Field of Classification Search
USPC ..... Plt./132
CPC ..... A01H 6/749; A01H 5/02
See application file for complete search history.

(56) References Cited

U.S. PATENT DOCUMENTS

| | | | |
|---|---|---|---|
| PP8,494 | P | 12/1993 | Tracy |
| PP9,389 | P | 12/1995 | Winchel |
| PP22,469 | P2 | 1/2012 | Carruth |
| PP22,571 | P2 | 3/2012 | Carruth |
| PP23,324 | P2 | 1/2013 | Bedard |
| PP23,692 | P3 | 7/2013 | Bedard |
| PP29,273 | P2 | 5/2018 | Fryer |

OTHER PUBLICATIONS

Weeks Roses: In Love Again, Wholesale Rose Catalog, Weeks Roses, 2025. Retrieved from the Internet: <URL:http://www.weeksroses.com/downloads/Catalogs_Digital/_WR25_Catalog_Digital.pdf>, 76 pages.

*Primary Examiner* — Keith O. Robinson
(74) *Attorney, Agent, or Firm* — McKee, Voorhees & Sease, PLC

(57) ABSTRACT

A new variety of Hybrid Tea rose suitable for garden decoration, having flowers of white with pink picotee coloration.

1 Drawing Sheet

Classification: The present disclosure relates to a new *Rosa hybrida* plant.

Variety denomination: The new plant has the varietal denomination 'WEKselyan'.

BACKGROUND OF THE INVENTION

This invention relates to a new and distinct variety of Hybrid Tea Rose. It has as its seed parent the variety known as 'HILaroma' (U.S. Plant Pat. No. 8,494) and as its pollen parent the variety known as 'WEKjoe' (U.S. Plant Pat. No. 9,389).

SUMMARY OF THE INVENTION

Among the features which distinguish the new variety from other presently available and commercial rose cultivars known to the applicant are the following combinations of characteristics: its elegant high centered flowers of white with pink picotee coloration, its abundant blooms, its excellent color stability throughout the life of the flower, its hairy peduncle and its vigorous growth. The plant has an upright somewhat spreading growing habit, suitable for outdoor garden decoration.

Asexual reproduction of the new variety by budding as performed in Kern County, California, shows that the foregoing and other distinguishing characteristics come true to form and are established and transmitted through succeeding asexual propagations. 'WEKselyan' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'HILaroma' by the following combination of characteristics: whereas 'WEKselyan' bears flowers of white with pink picotee coloration with a moderate fruity to citrus-like fragrance, 'HILaroma' bears flowers of Naples yellow strongly edged with Venetian pink coloration with a strong sweet and spicy fragrance. The new variety has an upright somewhat spreading medium height to moderately tall growing habit (about 127 to about 188 cm. in height), whereas the seed parent has a bushy upright significantly shorter growing habit (about 120 to about 130 cm. in height).

The new variety may be distinguished from its pollen parent, 'WEKjoe' by the following combination of characteristics: whereas 'WEKselyan' bears flowers with a moderate fruity to citrus-like fragrance, 'WEKjoe' bears flowers with a mild tea fragrance. The new variety has an upright somewhat spreading growing habit (about 76 to about 137 cm. spread at the widest point), whereas the pollen parent has an upright significantly wider (about 120 to about 185 cm. spread at the widest point) growing habit.

COMPARISON WITH THE CLOSEST COMMERCIALLY AVAILABLE CULTIVAR

The new variety may be distinguished from its closest commercially available cultivar, 'WEKpurmebep' (U.S.

Plant Pat. No. 28,720) by the following combination of characteristics: whereas 'WEKselyan' bears medium to large sized flowers (about 8.4 to about 13.9 cm. in diameter) with a moderate fruity to citrus-like fragrance, 'WEKpurmebep' bears smaller flowers (about 7.5 to about 11.2 cm. in diameter) with a moderate sweet pear with slight spicy fragrance. The new variety has an upright somewhat spreading growing habit (about 76 to about 137 cm. spread at the widest point), whereas the closest commercially available cultivar has an upright wider (about 122 to about 152 cm. spread at the widest point) growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, California in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, California in the month of November. Phenotypic expression may vary with environmental, cultural and climatic conditions, as well as differences in conditions of light and soil.

Flower

The new variety sometimes bears its flowers singly, sometimes in clusters of two to five or more per stem. Flowers may be borne in regular rounded clusters on strong moderately short to long stems (about 20 to about 102 cm.). The cluster ranges from about 12.5 to about 16.5 cm. in diameter. Outdoors, the plant blooms abundantly and nearly continuously during the growing season. The flowers have a moderate fruity to citrus-like fragrance.

Bud

The peduncle is about 2.6 to about 15.0 cm. in length, of average to somewhat heavy caliper (about 0.2 to about 0.5 cm. in diameter), and usually erect. It is smooth, with very few stipitate glands, and some hairs. Peduncle color is between 146C and 148B often heavily suffused, especially on the side exposed to the sun, with between 183B and 187B.

Before the calyx breaks, the bud is about 1.1 to about 2.1 cm. in diameter at the widest point, about 1.6 to about 2.7 cm. in length, and pointed to moderately ovoid in shape. The surface of the bud bears between 15 to 21 foliaceous appendages, usually with stout entire foliaceous parts extending beyond the tip of the bud about 3/4 or more of its length. Bud color is between 137C and 147B often lightly suffused, especially on the side exposed to the sun, with between 187A and 187B.

The sepals are 5 per flower, about 2.6 to about 8.2 cm. in length and about 0.6 to about 1.3 cm. in width at the widest point. The outer surface color of the sepal is between 137C and 147B often lightly suffused, especially on the side exposed to the sun, with between 187A and 187B. The outer surface of the sepal is smooth and bears between 0 to 9 foliaceous appendages with few hairs. The inner surface color of the sepal is near 145A broadly bordered by near 137C. After the sepals open, the inner surface color is often moderately suffused, especially on the area exposed to the sun, with between 187A and 187B. The inner surface of the sepal is covered with fine wooly tomentum; sepal margins are entire and lined with few stipitate glands and some hairs. The sepals are moderately permanent, and usually spear-shaped in shape with acute apices.

The receptacle of the flower is of short length (about 0.2 to about 0.5 cm.) and moderately thin to average in caliper (about 0.5 to about 0.8 cm. in diameter). The receptacle is cupped shape in form. Its surface is smooth with very few hairs and with moderately thick fleshy walls. The receptacle color is between 144A and 148B.

As the petals open (after the calyx breaks), the bud is about 1.9 to about 2.6 cm. in diameter at the widest point, about 3.0 to about 3.5 cm. in length, and pointed to somewhat ovoid in form. The color of the under and upper surfaces of the newly opened petals is between 1D and 154D often moderately blushed on the outermost petals with between 59B and 61A. There is no visible change in coloration at the point where the petal attaches.

Bloom

When fully open, the bloom ranges from about 8.4 to about 13.9 cm. in diameter. Petalage is double with about 23 to 36 petals and about 2 to 8 petaloids irregularly arranged. When partially open, the bloom form is moderately ovoid to high centered and somewhat cupped, and the petals are loosely spiraled to somewhat cupped with petal edges somewhat reflexed outward. When fully open, the bloom form is more cupped, and the petals are loosely cupped with petal edges somewhat reflexed outward.

Petals

The substance of the petals is moderately heavy and of moderately thin to medium thickness, with upper surfaces moderately satiny and under surfaces slightly shiny. The petals are about 3.5 to about 6.6 cm. in length and about 3.3 to about 7.1 cm. in width at the widest point. Petal margins are entire.

The outer petals are broadly rounded in shape with rounded apices.

The inner petals are broadly rounded to somewhat obovate in shape with rounded apices.

Petaloids are about 1.4 to about 5.7 cm. in length and about 0.6 to about 3.2 cm. in width at the widest point. Petaloids are irregularly shaped moderately obovate to somewhat oblanceolate and somewhat subulate with rounded apices to sometimes somewhat lacerated apices.

Newly opened flower

The under-surface color of the outer, intermediate and inner petals is between 8D and 155B often lightly blushed near the petal edge with between 61B and 66B. There is no visible change in coloration at the point where the petal attaches. The upper surface color of the outer, intermediate and inner petals is between 8D and 155B usually heavily blushed near the petal edge with between 61B and 66B. There is no visible change in coloration at the point where the petal attaches.

The under and upper surface colors of the petaloids are similar in coloration to the upper and under surfaces of the intermediate and inner petals.

The general tonality of the newly opened flower is between 8D and 155B usually heavily blushed near the petal edge with between 61B and 66B.

Three-day-old flower

The under-surface color of the outer, intermediate and inner petals is between 158B and 155B sometimes lightly blushed near the petal edge with between 64B and 66B. There is no visible change in coloration at the point where the petal attaches. The upper surface color of the outer, intermediate and inner petals is between 158B and 155B usually heavily blushed near the petal edge with between 64B and 66B. There is no visible change in coloration at the point where the petal attaches.

The under and upper surface colors of the petaloids are similar in coloration to the upper and under surfaces of the intermediate and inner petals.

The general tonality of the three-day-old flower is between 158B and 155B usually heavily blushed near the petal edge with between 64B and 66B.

On the spent bloom, the petals usually drop off cleanly.

In November in Wasco, California, blooms on the bush growing outdoors generally last about four to five days. Cut roses from plants grown outdoors and kept at normal indoor living temperatures generally last about four to five days.

Male reproductive organs

Stamens are many in number (average about 140) and are arranged regularly about the pistils; a few are mixed with petaloids. The filaments are of short to somewhat long length (about 0.4 to about 1.3 cm.) most with anthers. Filaments are between 7D and 9C in color sometimes lightly suffused with near 53B. The anthers are of medium to somewhat large size for the class and all open approximately at the same time. Anther color when immature is near 20A on the external part and near 18D on the internal part. Anther color at maturity is near 164B on the external part and near 200A on the internal part. Pollen is moderate and between 18B and 19C in color.

Female reproductive organs

Pistils vary in number (average about 170). The styles are uneven, moderately short to long in length (about 0.5 to about 1.1 cm.), somewhat thin to average in caliper, and loosely bunched to somewhat separated. Stigma color is between 21D and 20B. Style color is between 1D and 154D usually heavily suffused with between 60A and 60B. Ovaries are usually all enclosed in the calyx. The ovaries are of small to medium size and between 158A and 158B in color.

Hips are of average to somewhat long length (about 1.8 to about 2.4 cm.), rounded in form with a flat top, and between 25A and 28B in color when ripe. The hip surface is smooth with thick fleshy walls.

The seeds are irregularly rounded, smooth in texture, approximately 23 to about 56 per hip, about 0.2 to about 0.5 cm. in diameter at the widest point and between 165B and 164A in color.

Foliage

The compound leaves are usually comprised of three to seven leaflets and are borne abundantly. The seven-leaflet leaves are about 9.7 to about 19.2 cm. in length and about 7.4 to about 15.5 cm. in width at the widest point, leathery in texture on both sides, and moderately glossy in finish on the upper side and somewhat glossy in finish on the underside. The leaves have a pinnate venation pattern. The terminal leaflets are about 4.0 to about 9.7 cm. in length and about 2.1 to about 6.4 cm. in width at the widest point, shaped moderately oval to somewhat ovate with acute to somewhat acuminate apices and rounded to somewhat acute bases. Their margins are usually simply serrate.

The upper surface color of the mature leaf is between 139A and 147A. The under- surface color of the mature leaf is between 147B and 194C. The under and upper colors of the leaf veins on the mature leaf are similar in coloration to the upper and under surfaces colors of the mature leaf. The upper surface color of the young leaf is between 137B and 146A, usually heavily suffused with between 187B and 187A. The under-surface color of the young leaf is between 147C and 194C, usually heavily suffused with between 187B and 187C. The under and upper colors of the leaf veins on the young leaf are similar in coloration to the upper and under surfaces colors of the young leaf.

The rachis is about 3.8 to about 7.8 cm. in length, about 0.1 to about 0.2 cm in width at the widest point, and rough. The upper side is deeply grooved with few hairs and very few stipitate glands on the edges of the grooves. The under side of the rachis is rough with few hairs, very few stipitate glands and few small prickles. The rachis color is near 145B on the underside and near 146B on the upper side, often heavily suffused on the young leaves with between 183B and 187B.

The stipules are about 1.3 to about 2.4 cm. in length and of medium to somewhat wide width (about 0.4 to about 1.0 cm.) with somewhat short to medium length straight points that usually turn out at an angle of more than 45 degrees and sometimes recurve toward the stem. The under and upper surface color of the stipule is between 137C and 146B. The upper and under surfaces of the stipules are smooth in texture.

The petiole is somewhat light to average in caliper and rough. The upper side is deeply grooved with few hairs and very few stipitate glands on the edges of the grooves. The under side of the petiole is rough with few hairs, very few stipitate glands and few small prickles. The petiole is about 0.1 to about 1.5 cm. in length and about 0.1 to about 0.2 cm in width at the widest point. The petiole color is near 145B on the underside and near 146B on the upper side, often heavily suffused on the young leaves with between 183B and 187B.

The plant displays an average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, California. The plant's winter hardiness and drought/heat tolerance are yet to be determined.

Growth

The plant has an upright somewhat spreading medium height to moderately tall growing habit (about 127 to about 188 cm. in height and about 76 to about 137 cm. spread at the widest point), with moderately full branching. It displays very vigorous growth and the canes are of medium to moderately heavy caliper for the class (about 1.3 to about 3.2 cm. in diameter at the widest point).

The color of the major stems is between 146A and 147B. The major stems are rough in texture and they bear many large prickles that are about 0.6 to about 1.3 cm. in length. The large prickles are angled slightly downward with a moderately long narrow oval base; prickle color is between 165B and 164A sometimes lightly suffused with near 201D. The major stem bears few small prickles of similar shape and coloration.

The color of the branches is between 137C and 146B. The branches are rough in texture and they bear some large prickles which are of similar size and shape to the large prickles on the major stems; prickle color is between 161A and 162A often moderately suffused with between 187C and 187D. The branches bear few small prickles of similar shape and coloration.

The color of the new shoots is between 146C and 146B often heavily suffused with between 183A and 187B. The new shoots are rough in texture and they bear some large prickles which are of similar size and shape to the large prickles on the major stems; prickle color is between 152A and 152B often moderately suffused with between 187C and 187B. The shoots bear few small prickles of similar shape and coloration.

I claim:

1. A new and distinct Hybrid Tea rose plant of the variety designated 'WEKselyan' substantially as described and illustrated herein.

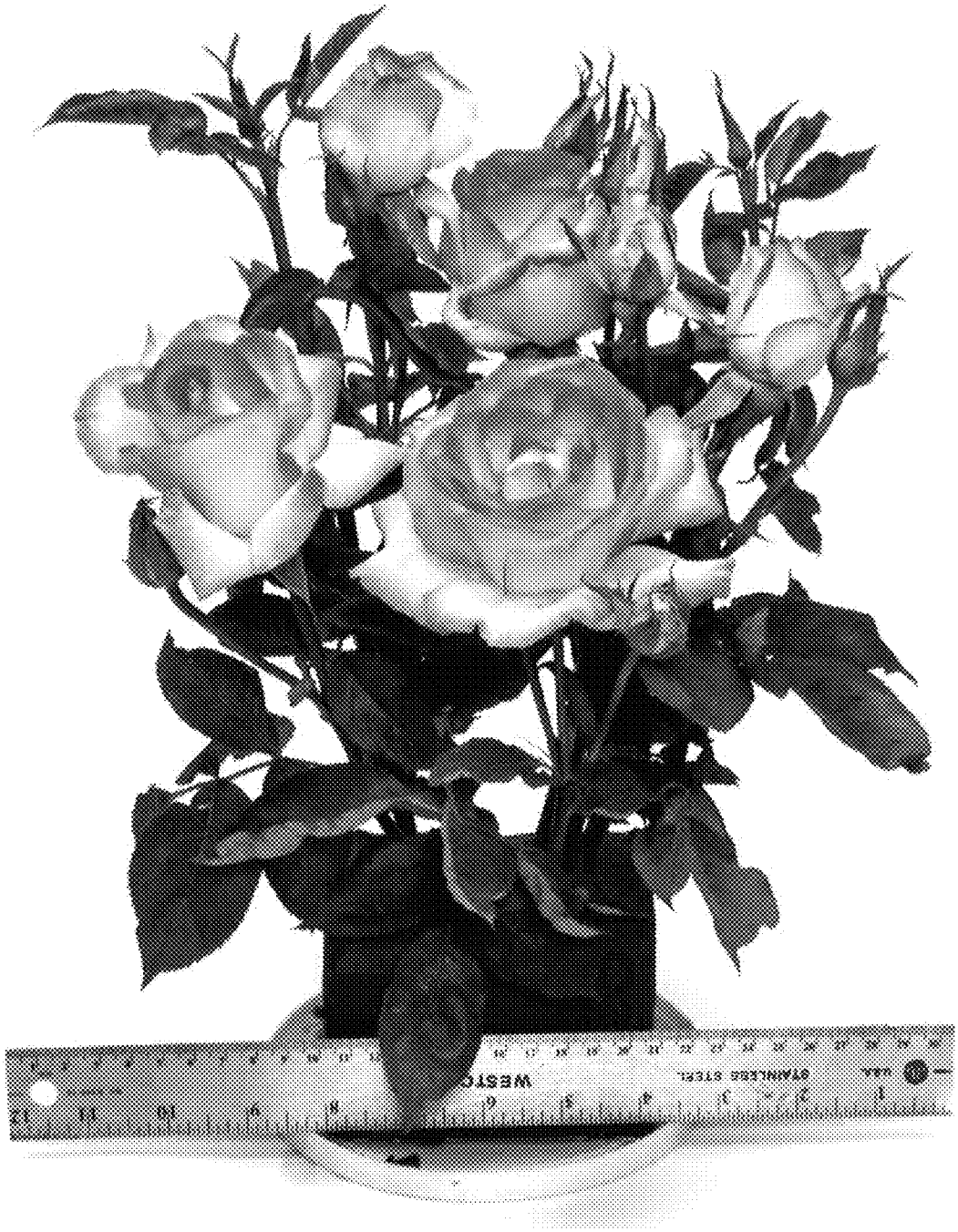

* * * * *